United States Patent [19]

Kandarpa

[11] Patent Number: 5,178,618
[45] Date of Patent: Jan. 12, 1993

[54] METHOD AND DEVICE FOR RECANALIZATION OF A BODY PASSAGEWAY

[75] Inventor: Krishna Kandarpa, Wayland, Mass.

[73] Assignee: Brigham and Womens Hospital, Boston, Mass.

[21] Appl. No.: 641,890

[22] Filed: Jan. 16, 1991

[51] Int. Cl.⁵ .............................................. A61B 17/38
[52] U.S. Cl. ........................................ 606/28; 606/41; 606/195; 606/198
[58] Field of Search ................. 606/41, 34, 27–29, 606/31, 191, 194, 195, 198

[56] References Cited

U.S. PATENT DOCUMENTS

| | | |
|---|---|---|
| 4,643,186 | 2/1987 | Rosen et al. |
| 4,674,481 | 6/1987 | Boddie, Jr. et al. |
| 4,709,698 | 12/1987 | Johnston et al. ................. 606/41 |
| 4,733,665 | 3/1988 | Palmaz |
| 4,790,311 | 12/1988 | Ruiz |
| 4,795,458 | 1/1989 | Regan ................................ 606/194 X |
| 4,799,479 | 1/1989 | Spears |
| 4,808,164 | 2/1989 | Hess |
| 4,877,030 | 10/1989 | Beck et al. |
| 4,979,518 | 12/1990 | Itoh et al. ........................ 606/28 X |

Primary Examiner—Lee S. Cohen
Attorney, Agent, or Firm—Sterne, Kessler, Goldstein & Fox

[57] ABSTRACT

The present invention relates to a method and device for the recanalization of an occluded blood vessel which includes an expandable wire-mesh stent or support and an external radio frequency (rf) energy source or other suitable heat generating device. The device of the present invention may also be used to recanalize other occluded body passageways or conduits.

28 Claims, 2 Drawing Sheets

METHOD AND DEVICE FOR RECANALIZATION OF A BODY PASSAGEWAY

FIELD OF THE INVENTION

The present invention relates to a support or stent for the recanalization of an occluded artery or other body passageway. More particularly the invention utilizes a heatable arterial support or stent to repair and prevent restenosis of an occluded blood vessel.

BACKGROUND OF THE INVENTION

When a patient is suffering from atherosclerosis, significant occlusions or blockages are formed on the interior wall of the artery. As a result of these occlusions, the organ or extremity to which blood is to be supplied is compromised and the patient may experience a myocardial infarction or stroke. Some forms of occlusions may be treated by drugs while others require surgery.

In the past, percutaneous transluminal balloon angioplasty (PTBA), dilation of the arterial wall by an inflatable balloon to restore blood flow, was an acceptable means of treatment for this condition and was considered to be a less invasive alternative to surgery. However, PTBA suffers from the disadvantage of a moderate rate of restenosis (the recurrence of blockage). It has been shown that approximately 30% of all patients who undergo balloon angioplasty redevelop the occlusion within three months due to the proliferation of cells lining the vessel wall and other atherogenic processes. Often, the wall of the dilated artery tends to spring back to its original shape following deflation of the dilation balloon. Arterial stenting has been introduced as a solution to this recoil of the vessel wall.

Arterial stenting involves the placement of an expandable coil spring or wire-mesh tube within the occluded artery to reopen the lumen of the blood vessel. One example of an arterial stent is disclosed in U.S. Pat. No. 4,739,762 to Julio Palmaz. The Palmaz device comprises an expandable wire-mesh graft or prosthesis which is mounted upon an inflatable balloon catheter. The catheter assembly, including the graft, is delivered to the occluded area and is then inflated to radially force the graft into contact with the occlusion. As the graft expands, the lumen of the blood vessel is opened and blood flow is restored. After complete expansion of the graft, the balloon catheter is deflated and removed, leaving behind the graft to buttress and prevent elastic recoil of the blood vessel wall.

Although this method is successful in preventing recoil of the vessel wall, restenosis does occur. Smooth muscle cells which form the vessel wall tend to proliferate and build-up in the newly stented area of the blood vessel. This cellular buildup eventually becomes great enough to block the lumen of the blood vessel.

It has recently been determined that localized heating of the blood vessel wall may prevent the proliferation of smooth muscle cells which are believed to cause restenosis. One example of localized blood vessel heating is disclosed in U.S. Pat. No. 4,799,479 to Spears. The Spears patent discloses an apparatus for angioplasty having an inflatable balloon catheter which is provided with a meshwork of electrical wires to supply heat to a vessel wall. Following balloon angioplasty, the external surface of the balloon is heated to fuse together disrupted tissue elements and to kill smooth muscle cells which are believed to lead to restenosis. Unfortunately, the Spears device does not adequately prevent the spontaneous elastic recoil of the arterial wall. Immediately following angioplasty, the arterial wall begins to spring back to its original shape.

Thus stenting in and of itself is ineffective in preventing restenosis due to the occurrence of cellular proliferation. Likewise, balloon dilation in combination with localized heating does not adequately prevent restenosis since the vessel wall tends to spontaneously return to its original occluded shape.

Accordingly, prior to the development of the present invention, there has been no effective treatment of atherosclerosis which also prevents restenosis of the once occluded blood vessel.

SUMMARY OF THE INVENTION

It is with this problem in mind that the present invention was developed. Unlike the prior art, the present invention is a device for permanent recanalization of an occluded blood vessel (or other body passageway) utilizing a stent in combination with a localized tissue heating means. The device includes a stent which is inserted into an occluded body passageway having sufficient radial resistance to recanalize the passageway and a means for heating the stent to a temperature between 50° C. and 100° C. The stent of the present invention may be constructed of metal and may be balloon expandable. Moreover, the stent may be biased to exert a radial force against the occluded passageway when inserted therein. The stent may be heated by a resistive heater, a laser radiation source, an optical fiber, or microwaves (having a frequency sufficient to couple to the material forming the stent).

The device of the present invention also includes a stent which is inserted into an occluded body passageway having sufficient radial resistance to recanalize the passageway and a means for heating the body passageway to a temperature between 50° C. and 100° C. The body passageway may be heated by an external radio frequency energy source which may include paired multiple feeder inductor rings positioned between a plurality of capacitor plates for producing a tuned radio frequency electromagnetic field.

Furthermore, the present invention includes a method for recanalizing an occluded body passageway comprising the steps of introducing a balloon catheter having a stent disposed about the catheter into a passageway to a location proximate an occlusion; expanding the balloon catheter thereby expanding the stent; applying heat to the stent; and removing the balloon catheter from the passageway. The stent for this method of recanalization may be metallic and may be biased to exert a radial force against the passageway. The stent may be heated to a temperature between 50° C. and 100° C. by a resistive heater, a laser radiation source, an optical fiber, or microwaves (having a frequency sufficient to couple to the material forming the stent).

The present invention also includes a method for recanalizing an occluded body passageway comprising the steps of introducing a balloon catheter having a stent disposed about the catheter into a passageway to a location proximate an occlusion; expanding the balloon catheter thereby expanding the stent; applying heat to the tissue of the passageway; and removing the balloon catheter from the passageway. The stent may be heated to a temperature between 50° C. and 100° C. by an external radio frequency energy source which may include paired multiple feed inductor rings positioned between a plurality of capacitor plates for producing a tuned radio frequency electromagnetic field.

BRIEF DESCRIPTION OF THE DRAWINGS

Various objects, features, and attendant advantages of the present invention will be more fully appreciated as the same becomes better understood from the following detailed description of the present invention when considered in connection with the accompanying drawings, in which.

DETAILED DESCRIPTION OF THE DRAWINGS

Figure 1:
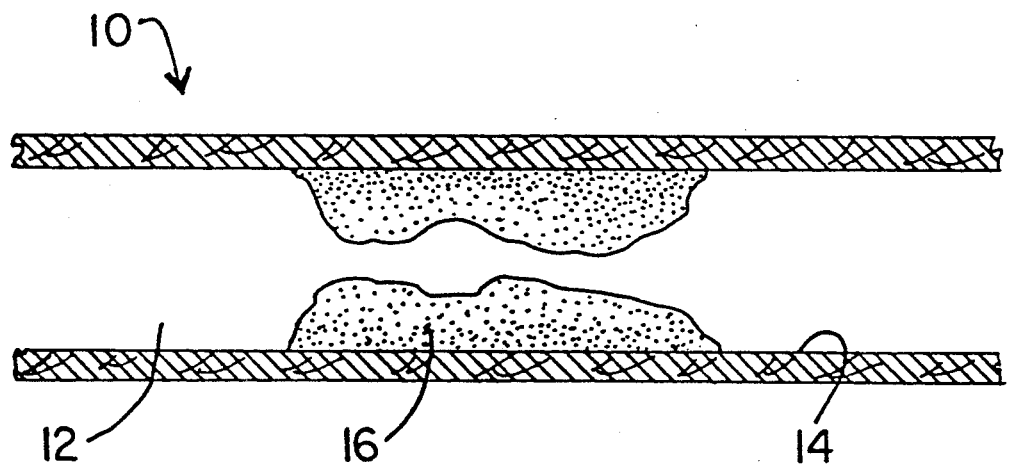
FIG. 1 is a longitudinal cross-sectional view of an occluded blood vessel.

With continuing reference to the drawing figures in which similar reference numerals are used throughout the description to describe similar features of the invention, a cross-sectional view of an occluded blood vessel is shown generally at 10 in FIG. 1. The interior wall 14 of blood vessel 10 is shown having an occlusion 16 which is deposited thereon. Occlusion 16 blocks the flow of blood which normally travels freely through the vessel central passageway or lumen 12.

Figure 2:
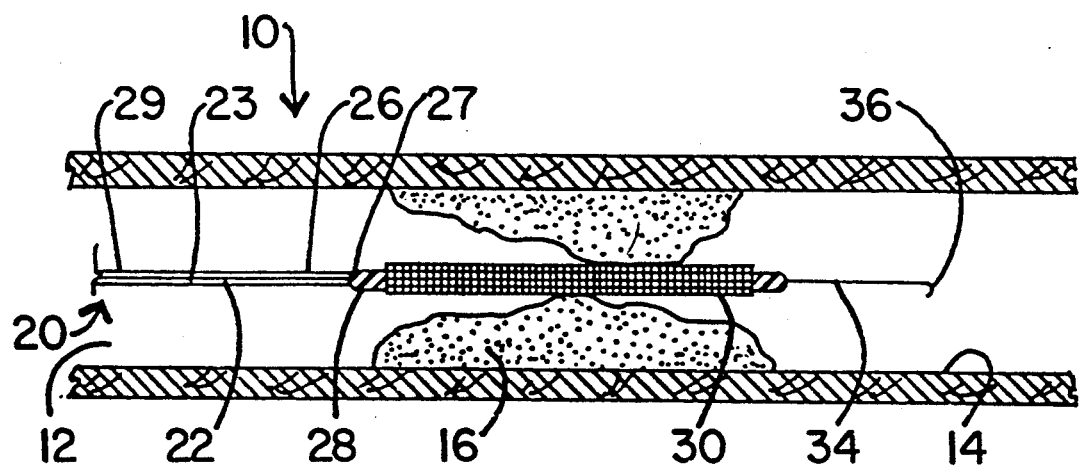
FIG. 2 is a schematic view of the catheter assembly of the present invention inserted within the occluded blood vessel shown in FIG. 1.

Turning now to FIG. 2, the device of the present invention for the recanalization of an occluded blood vessel is shown. The device generally includes an expandable tube like support or stent 30 and a means for heating the stent (shown at 43 in FIG. 4), each of which will now be described.

Catheter 20 is inserted into blood vessel 10 percutaneously using conventional catheter introduction techniques. Catheter 20 is cylindrical in shape and is constructed of a biologically compatible, flexible material such as polyethylene or any other suitable material which exhibits these characteristics. In its preferred embodiment, the outer diameter of catheter 20 is uniform throughout and is approximately 2 to 3 mm wide. It should be noted however that the outer diameter of balloon 28 may vary depending on the size of the blood vessel into which the catheter is to be inserted. In addition, the invention may also be used in anatomical environments other than a blood vessel. One of ordinary skill will recognize that the size of the catheter, and other components of the invention can be appropriately sized and shaped to accomplish the desired task.

Throughout its entire length, catheter 20 is provided with a central passageway or lumen 22 having a uniform inner diameter of approximately 1 mm. A standard guidewire 34 constructed of approximately 0.038" gauge wire or smaller passes through central lumen 22 to assist in the delivery of catheter 20 into occluded artery 10. The distal end 36 of guide wire 34 is slightly curved or bent to prevent accidental puncture of vessel wall 14 during catheter placement.

At its distal end 26, catheter 20 is provided with an inflatable balloon 28 which surrounds catheter 20 and is constructed of a highly elastic material such as polyethylene or any other suitable material which is capable of expanding and returning to its original shape. In its deflated state, balloon 28 is approximately 10 to 60 mm in length and approximately 2.5 to 3.5 mm in diameter. However, the balloon dimensions may vary depending upon the size of the occluded blood vessel. Balloon 28 should be constructed so as to have a length which is at least equal to the length of the vessel occlusion. A separate port or channel 29, which may pass along outer wall 23 of catheter 20, sealably engages with and opens into balloon 28 at 27. At the appropriate time, a radiographic liquid medium, such as diluted iodinated contrast medium or any other suitable radiographic medium is injected through port 29 to inflate balloon 28.

A tube-like support or stent 30, which may take the form of a biased, cylindrical, metallic cage or wire-mesh (linked) tube, completely surrounds inflatable balloon 28 and has a first diameter of 2.75 to 3.75 mm. The stent 30 is open at both ends and is, at the most, equal to the length of the balloon which the stent surrounds. However, as stated above with regard to balloon 28 of catheter 20, the length of stent 30 may vary depending upon the size of the arterial occlusion which the balloon/stent assembly is intended to bridge. Stent 30 is constructed in such a manner so that when a radial force is applied from within its interior, the stent will expand to a predetermined second diameter which is greater than said first diameter. Furthermore, the stent is constructed so that it will remain in its expanded state upon removal of the radial force. The stent or support is fabricated of a metal or other suitable material (such as plastic coated metal) which is biologically compatible, exhibits anti-thrombogenic characteristics and is electromagnetically conductive.

The apparatus disclosed in U.S. Pat. No. 4,739,762 to Julio Palmaz, the disclosure of which is incorporated herein by reference, exhibits the above-described characteristics and would thus be a suitable device for achieving the objectives of the present invention. Other suitable devices include the endoprosthesis disclosed in U.S. Pat. No. 4,877,030 to Beck, et al. and the Schneider "rolling membrane" stent manufactured by Schneider, USA (Minneapolis, MN 55441).

Figure 3:
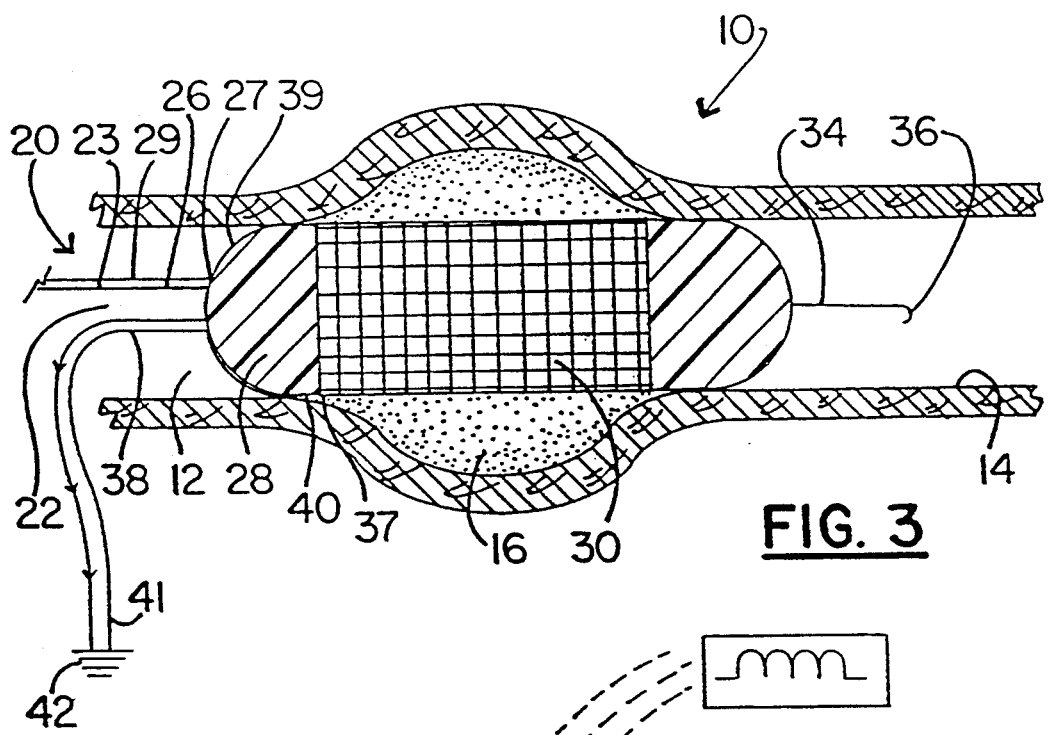
FIG. 3 is an enlarged view of the catheter assembly shown in FIG. 2, illustrating the balloon/stent assembly of the catheter in an expanded state.

With reference to FIG. 3, balloon 28 and stent 30 are shown in their respective expanded states within the occluded blood vessel. Notice that the force of the expanded balloon/stent assembly against occlusion 16 stretches the vessel wall 14 out of its normal shape.

As shown in FIG. 3, an insulated grounding wire 38, constructed of an electrically conductive material, such as steel, is secured to and passes along outer wall 23 of catheter 20 and external surface 39 of balloon 28. The distal end 40 of groundwire 38 is removably coupled with stent 30 at 37, while the proximal end 41 of guidewire 38 is grounded externally of the patient as at 42. It should be noted that groundwire 38 may pass anywhere along the outer wall of the catheter and balloon or within the central lumen of the catheter so long as it is removably coupled with stent 30 at its distal end 40. Furthermore, groundwire 38 may be coupled with stent 30 at any other suitable location which allows easy coupling and creates a good electrical contact.

The present invention is the use of a stent (for example, of the type described above) in combination with a heating means to recanalize an occluded blood vessel and to inhibit restenosis. In its preferred embodiment, the present invention includes a stent which is biased to exert a radial force against a body passageway and a radio frequency energy source to heat the tissue of an occluded blood vessel.

Figure 4:
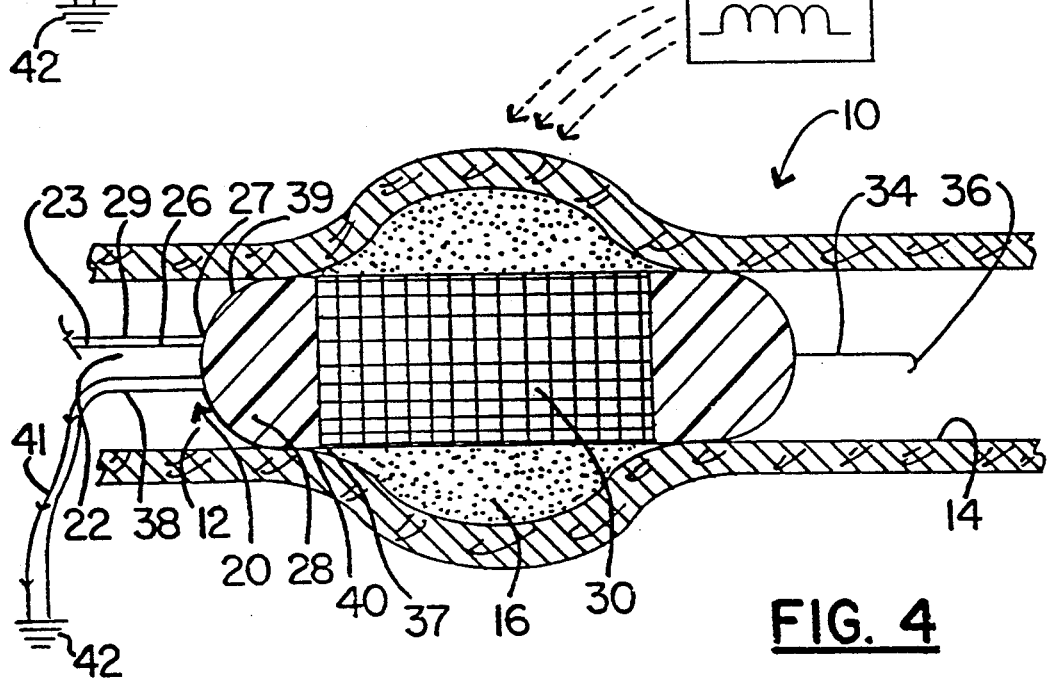
FIG. 4 is another view of the expanded balloon/stent assembly shown in FIG. 3, illustrating the expanded assembly subjected to an activated external radio frequency source.

Turning now to FIG. 4, the expanded balloon/stent assembly of FIG. 3 is shown subjected to an external radio frequency (rf) source 43, such as the RF Electromagnetic Field Generation apparatus disclosed in U.S. Pat. No. 4,674,481 to Bodie, Jr., et al, the disclosure of which is incorporated herein by reference. (It should be noted that an internal bipolar rf source may also be utilized.)

At the appropriate time, that is, when the stent has been fully expanded within the blood vessel, the external rf source is activated for a predetermined period of time to produce a predetermined temperature which will heat the tissues of the vessel wall. The preferred temperature for the destruction of smooth muscle cells is less than 100° C., approximately 50° C. The temperature for this procedure may be adjusted by increasing or decreasing the amplitude or frequency of the rf field. Although not shown, it is possible to place a temperature sensing device within the catheter to monitor heat generation.

When the rf source is activated for the proper time period, the alteration of the magnetic field of the surrounding blood vessel tissues produces heat generating eddy currents within the tissue. The expanded stent 30 and groundwire 38 (which are electromagnetically conductive) act as an electric sink for the electric current formed within the tissues. The heat generated within the tissues of the vessel wall 14 destroys the smooth muscle cells which are believed to lead to restenosis. The secondarily heated stent 30 also assists in the destruction by heating of smooth muscle cells. Upon completion of the heating procedure, groundwire 38 is disengaged from stent 30, balloon 28 of catheter 20 is deflated and the entire catheter assembly is removed from the blood vessel 10. Upon removal of the catheter, stent 30 remains in its expanded state and is left behind to support and prevent elastic recoil of the vessel wall 14. If needed, the heating treatment may be easily repeated by reinserting the groundwire into the blood vessel, recoupling it to the stent and activating the rf source for the appropriate time period.

It should be realized, however, that the stent proper of the present invention may be heated by other heat generating sources. These sources include: microwaves (having a wavelength sufficient to couple to the stent material), electrical resistive heaters, laser radiation sources or fiber optics. In those particular embodiments, stent 30 is directly heated by the heat generating source while the surrounding tissues of vessel wall 14 are heated by conduction. The result however is identical; the smooth muscle cells believed to cause restenosis are destroyed.

The device of the present invention is utilized in the following manner. The balloon catheter, having the stent in its unexpanded state disposed thereon, is introduced into the blood vessel or passageway via standard balloon catheter introduction methods. With the assistance of the guidewire, the catheter is located proximate the occlusion so that it is bridged by the balloon/stent assembly. The balloon portion of the catheter is then inflated by forcing a contrast medium into the balloon through the balloon inflation channel. The inflated balloon exerts a radial force upon the interior of the stent to expand it into its radially resistive state. The rf source (or other heat generating source) is then activated to heat the surrounding tissues (or stent) to destroy smooth muscle cells. Following the heating procedure, the groundwire is disengaged from the stent and the balloon catheter is deflated and removed, leaving behind the stent to permanently support the vessel wall. (Alternatively, the balloon catheter may be deflated and removed prior to heating of the blood vessel tissue.)

Thus the present invention not only recanalizes an occluded blood vessel, but destroys the smooth muscle cells which are believed to cause restenosis and provides a permanent support for the blood vessel wall to prevent elastic recoil thereof.

It should be realized that although the use of an external rf source was described, the heat generating sources listed above may be easily substituted and utilized to heat the stent of the present invention.

Furthermore, it should also be realized that the features and attendant advantages of the present invention are also applicable for use within other occluded body passageways or conduits. For example, the present invention may be introduced into a common bile duct occluded by a cancerous tumor. It has been shown that localized tissue heating in combination with radiation therapy is effective in destroying cancerous tissue cells. Thus, the catheter of the present invention, including the balloon/stent assembly, may be directed to the cancerous area of the common bile duct for localized tissue heating and cancer cell destruction purposes. The expanded stent may be permanently positioned within the common bile duct to canalize the cancerous area of the passageway.

The invention which is intended to be protected herein should not be construed as limited to the particular forms disclosed, as these are to be regarded as illustrative rather than restrictive. For example, the stent of the present invention may be provided with a heparin polymer to prevent coagulation. Additionally, the stent may be subjected to the radio frequency energy source available on magnetic resonance imaging (MRI) machines.

Variations and changes may be made by those skilled in the art without departing from the spirit of the invention. Accordingly, the foregoing detailed description should be considered exemplary in nature and not limited to the scope and spirit of the invention as set forth in the following claims.

What is claimed is:

1. A device for recanalization of an occluded body passageway, comprising:
   a stent, wherein said stent may be inserted into said occluded body passageway and has sufficient radial resistance to recanalize said passageway; and
   means for destroying cells of said body passageway which may reocclude the same by heating said stent to a temperature between 50° C. and 100° C.

2. The device of claim 1, wherein said stent is a balloon expandable stent.

3. The device of claim 1, wherein said stent is biased to exert a radial force against the passageway.

4. The device of claim 1, wherein said means for heating said stent is a resistive heater.

5. The device of claim 1, wherein said means for heating said stent generates microwaves at a frequency sufficient to couple to said stent.

6. The device of claim 1, wherein said means for heating said stent is a laser radiation source.

7. The device of claim 1, wherein said means for heating said stent is an optical fiber.

8. The device of claim 1, wherein said stent is metallic.

9. The device for recanalization of an occluded body passageway, comprising:
- a stent, wherein said stent may be inserted into said occluded body passageway and has sufficient radial resistance to recanalize said passageway; and
- a means for destroying cells of said body passageway which may reocclude the same by heating said body passageway to a temperature between 50° C. and 100° C.

10. The device of claim 9, wherein said stent is a balloon expandable stent.

11. The device of claim 9, wherein said stent is biased to exert a radial force against said body passageway.

12. The device of claim 9, wherein said means for heating said body passageway is a radio frequency source.

13. The device of claim 12, wherein said radio frequency source is external to said body passageway.

14. The device of claim 13, wherein said radio frequency source includes paired multiple feed inductor rings positioned between a plurality of capacitor plates for producing a tuned radio frequency electromagnetic field.

15. The device of claim 9, wherein said stent is metallic.

16. A method for recanalizing an occluded body passageway comprising the steps of:
a) introducing a balloon catheter having a stent disposed about said catheter into a passageway to a location proximate an occlusion;
b) expanding said balloon catheter thereby expanding said stent;
c) applying heat to said stent; and
d) removing said balloon catheter from said passageway.

17. The method of claim 16, wherein said stent is heated to a temperature between 50° C. and 100° C.

18. The method of claim 16, wherein said stent is biased to exert a radial force against the passageway.

19. The method of claim 16, wherein said heat is generated by a resistive heater.

20. The method of claim 16, wherein said heat is generated by microwaves at a frequency sufficient to couple to the material forming the stent.

21. The method of claim 16, wherein said heat is generated by a laser radiation source.

22. The method of claim 16, wherein said heat is generated by an optical fiber.

23. A method for recanalizing an occluded body passageway comprising the steps of:
a) introducing a balloon catheter having a stent disposed about said catheter into a passageway to a location proximate an occlusion;
b) expanding said balloon catheter thereby expanding said stent;
c) applying heat to the tissue of said passageway; and
d) removing said balloon catheter from said passageway.

24. The method of claim 23, wherein said stent is biased to exert a radial force against the passageway.

25. The method of claim 23, wherein said passageway is heated to a temperature between 50° C. and 100° C.

26. The method of claim 23, wherein said heat is generated by a radio frequency source.

27. The method of claim 26, wherein said radio frequency source is external to said passageway.

28. The method of claim 27, wherein said step of applying heat to the tissue of said passageway utilizes paired multiple feed inductor rings positioned between a plurality of capacitor plates to produce a tuned radio frequency electromagnetic field.

* * * * *